United States Patent [19]
Johnson

[11] 4,069,035
[45] Jan. 17, 1978

[54] 1-(2-CARBOXYARYL)-3-ARYL-1,2,4-TRIAZOLES AND USE AS HERBICIDES

[75] Inventor: Alexander Lawrence Johnson, Wilmington, Del.

[73] Assignee: E. I. Du Pont de Nemours and Company, Wilmington, Del.

[21] Appl. No.: 722,201

[22] Filed: Sept. 10, 1976

Related U.S. Application Data

[62] Division of Ser. No. 590,372, June 25, 1975.

[51] Int. Cl.$^2$ .......... A01N 5/00; A01N 9/22; C07D 249/08; C07D 401/04
[52] U.S. Cl. .......... 71/76; 8/1 D; 252/408; 71/78; 71/86; 71/90; 71/92; 260/294.8 R; 260/294.8 G; 260/294.9; 260/295 R; 260/295 CA; 260/308 R
[58] Field of Search .......... 260/308 R, 294.8 R, 260/294.8 G, 294.9, 295 CA, 295 R; 71/76, 90, 92, 82, 78, 86

[56] References Cited

U.S. PATENT DOCUMENTS

| | | | |
|---|---|---|---|
| 3,158,620 | 11/1964 | Klingsberg | 260/310 |
| 3,541,109 | 11/1970 | Kauer | 260/309 |
| 3,637,731 | 1/1972 | Johnson | 260/309 |

FOREIGN PATENT DOCUMENTS 2,600,655    1/1976    Germany.

*Primary Examiner*—Alton D. Rollins
*Attorney, Agent, or Firm*—Anthony P. Mentis

[57] ABSTRACT

Selected 1-(2-carboxyaryl)-4-arylimidazoles and 1-(2-carboxyaryl)-3-aryl-1,2,4-triazoles are useful in making buffer solutions; as picrate dyes; and as plant growth regulators. Exemplary are 1-(2-carboxyphenyl)-4-phenyl-imidazole and 1-(2-carboxyphenyl)-3-phenyl-1,2,4-triazole.

24 Claims, No Drawings

1-(2-CARBOXYARYL)-3-ARYL-1,2,4-TRIAZOLES AND USE AS HERBICIDES

This is a division, of application Ser. No. 590,372, filed June 25, 1975, allowed Feb. 22, 1977.

BACKGROUND OF THE INVENTION

Field of the Invention

Certain 1-(2-carboxyaryl)-4-arylimidazoles and 1-(2-carboxyaryl)-3-aryl-1,2,4-triazoles are useful in making buffer solutions; as picrate dyes; and as plant growth regulators.

PRIOR ART

U.S. Pat. No. 3,158,620 discloses certain 1,3- and 1,4-bis(aryl)pyrazoles for preparing azo dyes. German patent publication 2,219,702 shows certain 3,5-bis(aryl)-pyrazoles as plant growth regulators. U.S. Pat. No. 3,541,109 discloses 1-(2-carboxyphenyl)imidazoles for biological activity, and U.S. 3,637,731 shows 1-alkyl-phenylimidazoles, also for biological activity. None of the references disclose the compounds of this invention.

SUMMARY OF THE INVENTION

The invention embraces a compound of the formula:

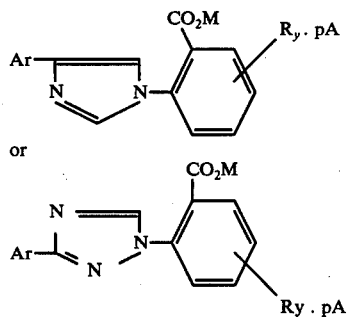

in which
- Ar is phenyl, naphthyl, biphenylyl, pyridyl, furyl, thienyl or phenyl substituted with up to two of fluorine, chlorine, bromine, iodine, alkyl of 1-5 carbons, methoxyl, trifluoromethyl, nitro, methylthio, trifluoromethoxyl, dimethylamino, cyano, acetyl, methylsulfonyl, carbamoyl or sulfamyl;
- R is hydrogen, fluorine, chlorine, bromine, iodine, methoxyl, trifluoromethyl, nitro, methylthio, trifluoromethoxyl or alkyl of 1-5 carbon atoms;
- $p$ is 0 or 1;
- $y$ is 1 or 2;
- A is an acid;
- M is hydrogen, sodium, potassium, lithium, calcium or magnesium; with the proviso that when M is other than hydrogen, $p$ is 0.

The compounds are useful as buffers, as picrate dyes and as plant growth regulators.

Preferred because of their good plant growth regulant activity are those compounds of the invention wherein Ar is phenyl, 4-chlorophenyl, 4-methoxyphenyl, 4-methylphenyl, and 3,4-dichlorophenyl.

More preferred are compounds of the preferred scope where M is hydrogen or alkali metal and R is hydrogen.

Preparation of the imidazoles I of the invention is illustrated by the general reaction

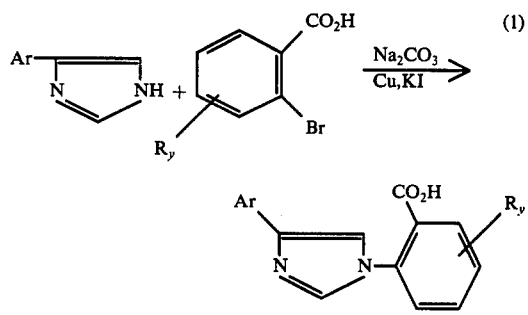

wherein Ar, R and $y$ have the meanings previously given. An appropriate 4-arylimidazole is heated at reflux with an appropriate 2-bromobenzoic acid in a suitable solvent such as dimethylformamide (DMF). Sodium carbonate in an amount of 2moles per mole of each starting material and catalytic amounts of potassium iodide and copper powder are also used in the reaction. This procedure follows that given by Johnson et al., *J. Med. Chem.* 12, 1024 (1969).

The reaction produces some of the isomeric 1-(2-carboxyaryl)-5-arylimidazole by virtue of the tautomerism:

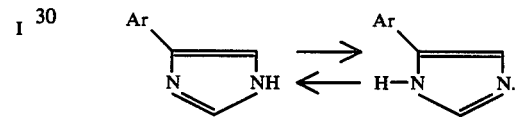

The compounds are named as though they are solely substituted 4-arylimidazoles and the invention includes both isomers.

The 4-arylimidazole starting materials in the above reaction are obtained by reaction of the appropriately substituted phenacyl bromide with formamide at reflux temperature, a procedure previously described by Bredereck, et al., Ber., 86, 88, 96 (1953).

Preparation of the triazoles II of the invention is illustrated by the general reaction

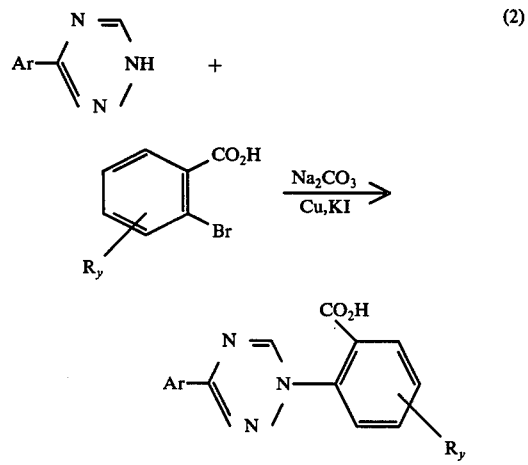

in which Ar, R and $y$ again are as previously defined. The reaction is essentially the same as general reaction (1) except that a 3-aryl-1,2,4-triazole is reacted with the 2-bromobenzoic acid.

This reaction can also produce some of the isomeric 1-(2-carboxyaryl)-5-aryl-1,2,4-triazole by virtue of the tautomerism:

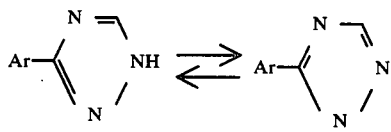

These compounds are also named as though they were solely substituted 3-aryl-1,2,4-triazoles and both isomers are included in the scope of the invention.

The 3-aryl-1,2,4-triazoles used as starting materials in general reaction (2) can be prepared by desulfurization of the corresponding 3-aryl-5-mercapto-1,2,4-triazoles with warm dilute nitric acid as follows:

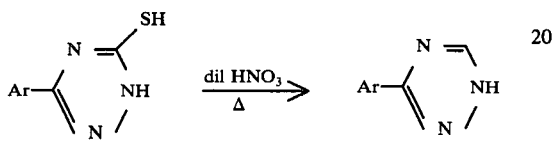

The reaction follows that given by Johnson et al. above, and also by W. Marckwald et al., Ber. 22, 568, 1353 (1889); ibid, 25, 2354 (1892).

The intermediate 3-aryl-5-mercapto-1,2,4-triazoles can be prepared by a two-step procedure starting with an appropriate aroyl chloride and thiosemicarbazide to produce a 1-aroylthiosemicarbazide intermediate:

The intermediate 1-aroylthiosemicarbazide can be cyclized by reaction with sodium methoxide in refluxing methanol for several hours; see E. Hoggarth, et al., J. Chem. Soc., 1160, 1163 (1949):

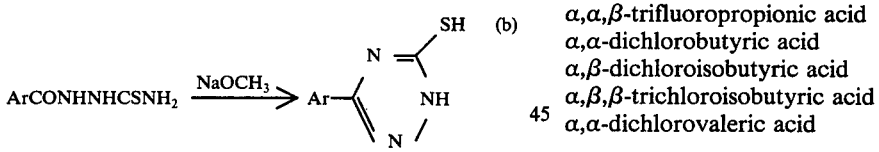

Use of an aroyl chloride with suitable substituents in the synthesis leads to 3-aryl-1,2,4-triazoles having the desired substituents.

"A" in the general formulas above is an acid which forms in acid addition compound with the imidazole or triazole of the invention. Included are inorganic acids such as HCl, $H_2SO_4$ and $HNO_3$, and organic acids such as acetic, citric and tartaric.

Preferred acids are halogenated aliphatic acids containing from 2 to 5 carbon atoms, halogenated benzoic acids, halogenated phenylacetic acids, halogenated phenoxyacetic acids, organic sulfonic acids, organic phosphoric acids, and inorganic phosphoric acids. These acids are preferred because the imidazole and triazole addition compounds formed from them are highly active as plant growth regulants and show good oil-solubility. Illustrative of these acids are:

2,3,5-trichlorobenzoic acid
2,3,6-trichlorobenzoic acid
2,3,5,6-tetrachlorobenzoic acid
2,3,5-triiodobenzoic acid
2-methoxy-3,6-dichlorobenzoic acid
2-methoxy-3,5,6-trichlorobenzoic acid
2-methyl-3,6-dichlorobenzoic acid
2,5-dichloro-3-aminobenzoic acid
2,5-dichloro-3-nitrobenzoic acid
2,3,6-trichlorophenylacetic acid
2,3,5,6-tetrachlorophenylacetic acid
2-methoxy-3,6-dichlorophenylacetic acid
2,4-dichlorophenoxyacetic acid
2,4,5-trichlorophenoxyacetic acid
phosphoric acid
methanephosphoric acid
phenylphosphoric acid Most preferred because of the grass-killing power and ease of preparation of their addition compounds are acids of the formula

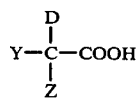

wherein D is halogen; Y is hydrogen, halogen, alkyl of from 1 to 3 carbon atoms, or haloalkyl; and Z is hydrogen, halogen or alkyl of 1 to 3 carbon atoms. Illustrative of these acids are:

chloroacetic acid
dichloroacetic acid
trichloroacetic acid
bromoacetic acid
dibromoacetic acid
tribromoacetic acid
trifluoroacetic acid
α,α-dichloropropionic acid
α,α-dibromopropionic acid
α,α,β-trichloropropionic acid
α,α,β-trifluoropropionic acid
α,α-dichlorobutyric acid
α,β-dichloroisobutyric acid
α,β,β-trichloroisobutyric acid
α,α-dichlorovaleric acid Also preferred because of the high activity of their imidazole and triazole addition compounds as foliage sprays are acids of the formula $R'SO_3H$, where R' is an aliphatic hydrocarbon radical, an aromatic hydrocarbon radical, or a halogen- or alkyl-substituted aromatic hydrocarbon radical. Illustrative of these acids are:

methanesulfonic acid
ethanesulfonic acid
dodecylsulfonic acid
benzenesulfonic acid
p-toluenesulfonic acid
dodecylbenzenesulfonic acid
2,4,6-trichlorobenzenesulfonic acid
naphthalene-β-sulfonic acid

SPECIFIC EMBODIMENTS OF THE INVENTION

The following are illustrative examples of the invention in which all parts and percentages are by weight and all degrees are Centrigrade unless otherwise stated.

General Procedure for Preparing 1-(2-Carboxyaryl)-4-Arylimidazoles

Preparation of 4-Arylimidazoles

A. 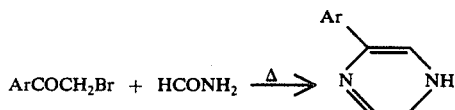

Using the general procedure of Bredereck et al. supra, the appropriate phenacyl bromide (0.10 mole) was stirred with formamide (125 ml) at reflux temperature (175°–180°) for two hours. The mixture was poured into 500 ml of dilute hydrochloric acid, and extracted with 2X fifty ml portions of chloroform; the aqueous layer was heated to boiling with decolorizing charcoal, filtered through diatomaceous earth, and the filtrate was cooled and made basic with concentrated ammonia to give the crude imidazole. The crude product was purified by recrystallization or sublimation. Several compounds prepared by this general procedure are given in Table I.

Table I

4-Arylimidazoles, 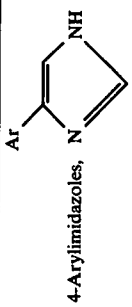

| Used in Preparing the compound of Example | Phenacyl-Bromide Starting Material | Product Structure Ar | Yield % | Purification | MP or BP | Formula | Calcd C | Calcd H | Analysis N | Found C | Found H | Found N | IR $\nu_{max}$ cm$^{-1}$ | UV $\lambda_{max}^{EtOH}$ ($\epsilon_{max}$) | NMR $\delta_{ppm}$ | |
|---|---|---|---|---|---|---|---|---|---|---|---|---|---|---|---|---|
| 1 | $C_6H_5COCH_2Br^d$ | $C_6H_5$ | | | | | | | | | | | | | | |
| 2 | 4-$ClC_6H_4COCH_2Br$ | 4-$ClC_6H_4$ | 76 | Subl. 170° (0.5 mm) | 140-141° | $C_9H_7ClN_2$ | 60.51 | 3.95 | 15.69 | 60.52 | 4.24 | 15.20 | 3460,1480$^a$ | 266(18,040) | 7.65(d J = 9)<br>7.30(d J = 9)<br>7.62(s)<br>7.28(s)<br>7.08(b) | $C_6H_4^c$<br>$H_2$<br>$H_3$<br>NH<br>NH$^c$ |
| 3 | 4-$CH_3OC_6H_4COCH_2Br$ | 4-$CH_3OC_6H_4$ | 61 | Subl. 145° (0.1 mm) | 134-135° | $C_{10}H_{10}N_2O$ | 68.95 | 5.79 | 16.08 | 68.84<br>68.86 | 5.91<br>5.90 | 15.67<br>15.94 | 3460,1500$^a$ | 264(18,640) | 8.38(b)<br>7.58(d J = 9)<br>6.85(d J = 9)<br>7.58(s)<br>7.18(s)<br>3.72(s) | $C_6H_4$<br>$H_2$<br>$H_3$<br>OCH$_3$<br>NH$^c$<br>$H_2$ |
| 4 | 4-$CH_3C_6H_4COCH_2Br$ | 4-$CH_3C_6H_4$ | 65 | Subl. 145° (0.25 mm) | 98-100° | $C_{10}H_{10}N_2$ | 75.92 | 6.37 | 17.71 | 75.07 | 6.37 | 17.33 | 3460,1510$^b$ | 261(16,780) | 12.28(s)<br>7.63(t J = 1)<br>7.60(d J = 8)<br>7.16(d J = 8)<br>7.28(s)<br>2.30(s) | $C_6H_4$<br>$H_3$<br>CH$_3$ |

$^a$CHCl$_3$ solution;
$^b$KBr;
$^c$CDCl$_3$/internal tetramethylsilane
$^d$Purchased from Aldrich Chemical Co.

Reaction of a 4-Arylimidazole with a 2-Bromobenzoic Acid

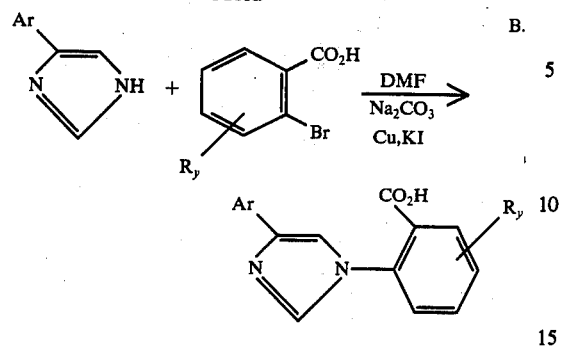

Using the general procedure of Johnson et al. supra, a mixture of the appropriate 4-arylimidazole (50 millimoles), 2-bromobenzoic acid (50 millimoles), anhydrous sodium carbonate (11.0 g, 103 millimoles), DMF (50 ml), copper powder (0.25 g) and potassium iodide (0.25 g) was stirred under reflux overnight. The reaction mixture was poured into water and acidified to pH 5 with acetic acid, cooled, and filtered to isolate the crude 4-aryl-1-(2-carboxyphenyl)imidazole. The crude product was usually purified by recrystallization from mixtures of ethanol, dimethylsulfoxide, and water.

Using the 4-arylimidazoles of Table I in the above general reaction the 1-(2-carboxyaryl)-4-arylimidazoles of Table II were prepared.

Table II 1-(2-Carboxyphenyl)-4-Arylimidazoles

| Example | Product Structure, Ar | Yield % | Purification Recrystallization Solvent | MP | Formula | Calcd C | Calcd H | Calcd N | Found C | Found H | Found N | IR $\nu_{max}^{KBr} cm^{-1}$ | UV $\lambda_{max}^{EtOH}(\epsilon_{max})$ | NMR $\delta_{ppm}$(dmso-$d_6$) |
|---|---|---|---|---|---|---|---|---|---|---|---|---|---|---|
| 1 | $C_6H_5$ | 76 | EtOH | 235–236° dec | $C_{16}H_{12}N_2O_2$ | 72.71 | 4.58 | 10.60 | 72.61 | 4.45 | 10.68 | 1700,1590 | 260(18,760) | 11.67 $CO_2H$ 8.17–6.88(m) aromatic |
| 2 | 4-Cl$C_6H_4$ | 43 | EtOH:dmso:$H_2O$ | 252–254° dec | $C_{16}H_{11}N_2O_2Cl$ | 64.33 | 3.71 | 9.38 | 64.90 | 4.00 | 9.30 | 1705,1600 | 267(22,940) | 8.17–7.27(m) aromatic |
| 3 | 4-$CH_3OC_6H_4$ | 49 | EtOH:dmso:$H_2O$ | 242–243° dec | $C_{17}H_{14}N_2O_3$ | 69.37 | 4.80 | 9.52 | 68.52 | 4.88 | 9.60 | 1700,1600 | 263(21,130) | 8.17–6.67(m) aromatic 3.78(s) $OCH_3$ |
| 4 | 4-$CH_3C_6H_4$ | 50 | EtOH:$H_2O$ | 200–202° dec | $C_{17}H_{14}N_2O_2$ | 73.36 | 5.07 | 10.07 | 70.08 | 5.04 | 10.14 | 1700,1600 | 261(20,540) | 8.17–6.33(m) aromatic 2.32(s) $CH_3$ |

General Procedure for Preparing
1-(2-Carboxyaryl)-3-Aryl-1,2,4-Triazoles
Preparation of 1-Aroylthiosemicarbazides

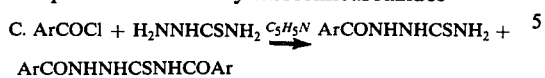

C. ArCOCl + H$_2$NNHCSNH$_2$ $\xrightarrow{C_5H_5N}$ ArCONHNHCSNH$_2$ + ArCONHNHCSNHCOAr The general procedure of E. Hoggarth was used (*J. Chem. Soc.*, 1160, 1163 (1949)). A mixture of powdered thiosemicarbazide (18.2 g, 0.20 moles) and dry pyridine (100 ml) was stirred at −5° and treated dropwise with the appropriate acid chloride (0.20 mole). After the mixture had been stirred overnight at 25°, it was poured into 500 ml of water and filtered. The desired 1-aroylthiosemicarbazide was readily separated from the small amount of 1,4-bis(aroyl)-thiosemicarbazide by recrystallization.

Several compounds prepared by this reaction are listed in Table III.

Table III
1-Aroylthiosemicarbazides, ArCONHNHCSNH$_2$

| Used in Preparing the compound of Example | Starting Material | Product Structure Ar | Yield % | Purification Recrystallization Solvent | MP | Formula | Analysis Calcd. C | H | N | Found C | H | N | IR $\nu_{max}^{KBr}$ cm$^{-1}$ | UV $\lambda_{max}^{EtOH}$ cm$^{-1}$ | NMR $\delta_{ppm}$(dmso-d$_6$) |
|---|---|---|---|---|---|---|---|---|---|---|---|---|---|---|---|
| 5 | C$_6$H$_5$COCl | C$_6$H$_5$ | 50–58$^a$ | H$_2$O | 196–198° | C$_8$H$_9$N$_3$OS | 49.23 | 4.65 | 21.53 | 49.42 49.50 | 4.68 4.48 | 20.75 | 3270, 3180, 1665,1600 | 245(17 235) | 10.17, 9.17 NH 7.88–7.23 C$_6$H$_5$, NH$_2$ |
| 6 | 4-ClC$_6$H$_4$COCl | 4-ClC$_6$H$_4$ | 65$^b$ | EtOH | 216–217° | C$_8$H$_8$N$_3$ClOS | 41.83 | 3.51 | 18.30 | 41.96 41.76 | 3.93 3.81 | 16.60 16.38 | 3610, 3280, 3180, 1675, 1590 | 318(4480) 245(19,260) | 10.5, 9.35 NH 7.93(d J = 8), C$_6$H$_4$ 7.53(d J = 8) |
| 7 | 3,4-Cl$_2$C$_6$H$_3$COCl | 3,4-Cl$_2$C$_6$H$_3$ | 44 | 3:1 EtOH:DMSO | 167–169° dec. | C$_8$H$_7$N$_3$Cl$_2$OS | 36.38 | 2.67 | 15.91 | 36.96 | 3.12 | 14.61 | 3420, 3240, 3150, 1675, 1615 | 290(3330) 280(3880) | 7.67, 3.4 NH 11.5, 9.48 NH 8.23–7.67 C$_6$H$_3$, NH$_2$ |
| 8 | 4-CH$_3$OC$_6$H$_4$COCl | 4-CH$_3$OC$_6$H$_4$ | 72 | aqu. EtOH | 230–231° | C$_9$H$_{11}$N$_3$O$_2$S | 48.00 | 4.92 | 18.66 | 48.16 47.90 | 4.94 5.05 | 18.27 18.28 | 3380, 3260, 3150, 1670, 1620, 1605 | 244(18,000) 254(24,100) | 10.25, 9.30 NH 7.90(d J = 8), 7.00(d J = 8) C$_6$H$_4$ 7.65 NH$_2$, 3.82(s) OCH$_3$ |
| 9 | 4-CH$_3$C$_6$H$_4$COCl | 4-CH$_3$C$_6$H$_4$ | 35 | EtOH | 214–216° | C$_9$H$_{11}$N$_3$OS | 51.67 | 5.30 | 20.09 | 51.70 51.94 | 5.38 5.47 | 19.81 19.92 | 3350, 3260, 3180, 1685, 1610 | 274(22,800) | 10.15, 9.27 NH, NH$_2$ 7.73(d J = 8), 7.17(d J = 8) C$_6$H$_4$ 7.57 NH 2.20(s) CH$_3$ |

$^a$A 5% yield of 1,4-bisbenzoylthiosemicarbazide, mp 172–174° (aq. EtOH) was also obtained.
$^b$A 50% yield of 1,4-bis(4-chlorobenzoyl)thiosemicarbazide, mp 262° dec (aq. EtOH) was also obtained, NMR spectrum; δ 10.58 (s, NH); 8.23–7.52 (m, C$_6$H$_4$); 3.33 (NH).

Preparation of 3-Aryl-5-Mercapto-1,2,4-Triazoles

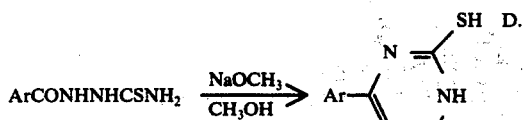

Hoggarth's procedure was followed. The appropriate 1-aroylthiosemicarbazide (0.10 mole) was stirred with methanol (250 ml) and sodium methoxide (16.2 g, 0.30 mole) at reflux temperature overnight. The mixture was evaporated to dryness, the residue was dissolved in hot water, treated with decolorizing carbon, and the filtrate was acidified with acetic acid to give the crude 3-aryl-5-mercapto-1,2,4-triazole. The crude product was usually recrystallized from aqueous ethanol.

Compounds prepared in this way are shown in Table IV.

Table IV

3-Aryl-5-mercapto-1,2,4-triazoles, $$\text{Ar} \underset{N}{\overset{N}{\diagdown}} \underset{N}{\overset{SH}{\diagup}} \underset{NH}{\diagdown}$$

| Used in Preparing the compound of Example | Aroylthio-semicarbazide Starting Material Ar | Product Structure Ar | Yield % | Purification Recrystallization Solvent | MP | Formula | Analysis Calcd. | | | Found | | | IR $\nu_{max}^{KBr}\text{cm}^{-1}$ | UV $\lambda_{max}^{EtOH}(\epsilon_{max})$ | NMR $\delta_{ppm}$(dmso-d$_6$) |
|---|---|---|---|---|---|---|---|---|---|---|---|---|---|---|---|
| | | | | | | | C | H | N | C | H | N | | | |
| 5 | C$_6$H$_5$ | C$_6$H$_5$ | 90 | 10% EtOH | 260° dec. | C$_8$H$_7$N$_3$S | 54.23 | 3.98 | 23.72 | 54.57 / 54.58 | 4.09 / 3.97 | 24.05 / 24.01 | 1610, 1590 1570 | 283(9020) 256(16,475) | 8.00–7.77, 2 protons 7.65–7.33, 3 protons 3.48 NH 13.33 SH, NH |
| 6 | 4-ClC$_6$H$_4$ | 4-ClC$_6$H$_4$ | 78 | 67% EtOH | 294–298° | C$_8$H$_6$N$_3$ClS | 45.39 | 2.86 | 19.85 | 45.25 | 2.93 | 19.67 | 1610, 1580, | 224(13,270) 296(9570) | 8.08(d J = 8) 7.68(d J = 8) }C$_6$H$_4$ |
| 7 | 3,4-Cl$_2$C$_6$H$_3$ | 3,4-Cl$_2$C$_6$H$_3$ | 48 | aqu. EtOH | 294–300° | C$_8$H$_5$Cl$_2$N$_3$S | 39.04 | 2.05 | 17.07 | 45.46 / 39.16 / 39.52 | 2.99 / 2.08 / 2.10 | 19.98 / 16.76 / 16.76 | 1560 1600, 1580 1550 | 255(21,380) 307(8515) 255(21,830) | 14.03 SH, NH 8.30(d J = 2) H$_2$ 8.08(d J = 8, each member d J = 2) H$_6$ 7.85(d J = 8) H$_5$ 11.33 SH, NH |
| 8 | 4-CH$_3$OC$_6$H$_4$ | 4-CH$_3$OC$_6$H$_4$ | 67 | aqu. EtOH + dmso mixture | 260–262° | C$_9$H$_9$N$_3$OS | 52.17 | 4.38 | 20.28 | 52.52 / 52.15 | 4.51 / 4.52 | 20.09 / 19.90 | 3250, 1620, 1565, 1525 | 283(14,200) 256(21,550) | 7.82(d J = 8) 6.95(d J = 8) }C$_6$H$_4$ 3.72(s) OCH$_3$ 13.77 SH, NH |
| 9 | 4-CH$_3$C$_6$H$_4$ | 4-CH$_3$C$_6$H$_4$ | 86 | aqu. EtOH | 267–269° dec. | C$_9$H$_9$N$_3$S | 56.54 | 4.75 | 21.98 | 56.70 / 56.48 | 4.79 / 4.83 | 21.61 / 21.65 | 1620, 1590 1565, 1525 | 285(10,950) 254(18,790) 230(14,015) | 7.88(d J = 8) 7.37(d J = 8) }C$_6$H$_4$ 2.35(s) CH$_3$ |

Preparation of 3-Aryl-1,2,4-Triazoles

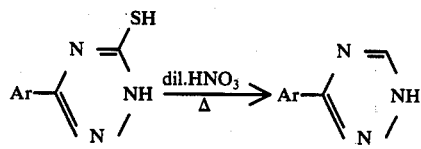

The general procedure of W. Marckwald, et al. (*Ber.*, 22, 568, 1353 (1889); ibid, 25, 2354 (1892)) was employed. A mixture of 3-aryl-5-mercapto-1,2,4-triazole (0.08 mole) and 80 ml of 20–25 percent nitric acid was warmed in a 2-liter Erlenmeyer flask on a steam bath for 10–15 minutes, by which time $NO_2$ evolution had usually ceased. The mixture was cooled, made basic to pH 9 with concentrated aqueous ammonia, and extracted with chloroform to give the crude 3-aryl-1,2,4-triazole. The crude product was purified by sublimation or recrystallization.

Several compounds prepared in this way are shown in Table V.

E.

Table V

3-Aryl-1,2,4-triazoles, Ar—⟨triazole with N=N, NH⟩

| Used in Preparing the compound of Example | Starting Material Ar | Product Structure Ar | Yield % | Purification | MP | Formula | Analysis Calcd. | | | Analysis Found | | | IR $\nu_{max}^{KBr}$cm$^{-1}$ | UV $\lambda_{max}^{EtOH}(\epsilon_{max})$ | NMR $\delta_{ppm}$(dmso-d$_6$) |
|---|---|---|---|---|---|---|---|---|---|---|---|---|---|---|---|
| | | | | | | | C | H | N | C | H | N | | | |
| 5 | C$_6$H$_5$ | C$_6$H$_5$ | 73–79 | Subl. 150° (0.1 mm) | 108–109° | C$_8$H$_7$N$_3$ | 66.19 | 4.86 | 28.95 | 65.83 / 65.85 | 4.97 / 4.99 | 29.66 / 29.52 | 3440, 1610, 1560, 1520, 1470[a] | 245(14,110) 242(14,360) | 12.75 NH<br>8.17(s) triazole proton<br>8.13–7.37(m) C$_6$H$_5$[b]<br>8.58(s) triazole proton |
| 6 | 4-ClC$_6$H$_4$ | 4-ClC$_6$H$_4$ | 57 | Rexd. EtOH | 188–189° | C$_8$H$_6$N$_3$Cl | 53.49 | 3.37 | 23.40 | 53.40 | 3.51 | 23.21 | 1610, 1570, 1495, 1470 | 252(19,400) 248(19,220) | 8.17(d J = 9)<br>7.55(d J = 9) }C$_6$H$_4$ |
| 7 | 3,4-Cl$_2$C$_6$H$_3$ | 3,4-Cl$_2$C$_6$H$_3$ | 69 | Rexd. EtOH | 172–174° | C$_8$H$_5$N$_3$Cl$_2$ | 44.89 | 2.36 | 19.63 | 39.83 | 2.40 | 17.64 | 1600, 1560, 1540, 1470 | 256(14,600) | 8.57(s) triazole proton<br>8.17–7.87(m) H$_2$,H$_3$<br>7.67(d J = 9), each a doublet J = 2) H$_6$ |
| 8 | 4-CH$_3$OC$_6$H$_4$ | 4-CH$_3$OC$_6$H$_4$ | 51 | Rexd. MeOH | 183–184° | C$_9$H$_9$N$_3$O | 61.70 | 5.18 | 23.99 | 61.70 / 61.51 | 5.33 / 5.34 | 24.23 / 24.21 | 1615, 1580, 1510, 1470 | 256(19,270) | 10.03 NH<br>8.43(a) triazole proton<br>8.00(d J = 8)<br>7.07(d J = 8) }C$_6$H$_4$<br>3.83(s) OCH$_3$ |
| 9 | 4-CH$_3$C$_6$H$_4$ | 4-CH$_3$C$_6$H$_4$ | 66 | Subl. 160° (0.25 mm) | 152–154° | C$_9$H$_9$N$_3$ | 67.90 | 5.70 | 26.40 | 62.48 | 5.71 | 27.13 | 1620, 1570, 1510, 1470 | 249(16,080) 245(15,920) | 8.57(s) triazole proton<br>8.07(d J = 8)<br>7.40(d J = 8) }C$_6$H$_4$<br>2.38(s) CH$_3$ |

[a] IR measured in CHCl$_3$
[b] NMR measured in CDCl$_3$

Reaction of a 3-Aryl-1,2,4-Triazole with a 2-Bromobenzoic Acid

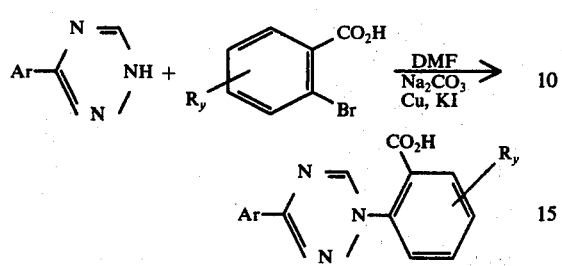

F.

Using the general procedure of Johnson et al. supra, 2-bromobenzoic acid was reacted with an appropriate 3-aryl-1,2,4-triazole to produce the desired 1-(2-carboxyphenyl)-3-aryl-1,2,4-triazoles. The procedure steps were as outlined above under reaction B.

Examples of compounds prepared in this way are listed in Table VI.

Table VI 1-(2-Carboxyphenyl)-3-aryl-1,2,4-triazoles,

| | 3-Aryl-1,2,4-Triazole Starting Material | Product Structure | | Purification Recrystallization | | | | Analysis | | | | | | | |
|---|---|---|---|---|---|---|---|---|---|---|---|---|---|---|---|
| | | | | | | | | Calcd. | | | Found | | | | |
| Example | Ar | Ar | Yield % | Solvent | MP | Formula | | C | H | N | C | H | N | IR $\nu_{max}^{KBr}$ cm$^{-1}$ | UV $\lambda_{max}^{EtOH}$ ($\epsilon_{max}$) | NMR $\delta_{ppm}$(dmso-d$_6$) |
| 5 | C$_6$H$_5$ | C$_6$H$_5$ | 57 | aqu. EtOH | 247° dec. | C$_{15}$H$_{11}$N$_3$O$_2$ | | 67.91 | 4.18 | 15.84 | 67.79 / 67.90 | 4.23 / 4.28 | 16.10 / 16.22 | 3440, 1705 | 248(19,440) | 8.90 CO$_2$H / 8.17–7.33(m) aromatic protons |
| 6 | 4-ClC$_6$H$_4$ | 4-ClC$_6$H$_4$ | 53 | aqu. EtOH:DMSO mixture | 246–247° dec. | C$_{15}$H$_{10}$N$_3$O$_2$Cl | | 60.11 | 3.36 | 14.02 | 57.95 | 3.35 | 13.62 | 1710 | 257(22,540) | 8.5–7.17(m) aromatic protons |
| 7 | 3,4-Cl$_2$C$_6$H$_3$ | 3,4-Cl$_2$C$_6$H$_3$ | 35 | aqu. EtOH:DMSO mixture | 263–264° dec. | C$_{15}$H$_9$N$_3$O$_2$Cl$_2$ | | 53.91 | 2.72 | 12.57 | 53.70 | 2.93 | 12.57 | 1705 | 261(23,520) | 8.33–7.50(m) aromatic protons |
| 8 | 4-CH$_3$OC$_6$H$_4$ | 4-CH$_3$OC$_6$H$_4$ | 39 | EtOH | 202–203° dec. | C$_{16}$H$_{13}$N$_3$O$_3$ | | 65.08 | 4.44 | 14.23 | 64.87 | 4.50 | 14.07 | 1710 | 263(22,030) | 8.33–7.07(m) aromatic, CO$_2$H protons / 3.83(s) OCH$_3$ |
| 9 | 4-CH$_3$C$_6$H$_4$ | 4-CH$_3$C$_6$H$_4$ | 48 | aqu. EtOH:DMSO mixture | 222–223° | C$_{16}$H$_{13}$N$_3$O$_2$ | | 68.80 | 4.69 | 15.05 | 66.85 | 4.71 | 14.60 | 1700 | 255(20,950) | 8.33–7.00(m) aromatic protons / 2.35(s) CH$_3$ |

Replacement of 2-bromobenzoic acid in reaction B with a substituted 2-bromobenzoic acid gives the correspondingly substituted 1-(2-carboxyaryl)-4-arylimidazoles as summarized in Table VII.

Table VII

| Example | 4-Arylimidazole Reactant Ar | Substituted 2-Bromobenzoic Acid | 1-(2-Carboxyaryl)-4-arylimidazole Product |
|---|---|---|---|
| 10 | phenyl | 2-bromo-4-methyl-benzoic acid | 1-(2-carboxy-5-methylphenyl)-4-phenylimidazole |
| 11 | phenyl | 2-bromo-4-n-propyl-benzoic acid | 1-(2-carboxy-5-n-propylphenyl)-4-phenylimidazole |
| 12 | 2-ethylphenyl | 2-bromo-4-t-butyl-benzoic acid | 1-(2-carboxy-5-t-butylphenyl)-4-(2-ethylphenyl)-imidazole |
| 13 | 2-methyl-4-chlorophenyl | 2-bromo-4-n-amyl-benzoic acid | 1-(2-carboxy-5-n-amylphenyl)-4-(2-methyl-4-chlorophenyl)-imidazole |
| 14 | 3-n-butylphenyl | 2-bromo-3,5-dichloro-benzoic acid | 1-(2-carboxy-4,6-dichlorophenyl)-4-(3-n-butylphenyl)-imidazole |
| 15 | 2,5-dibromophenyl | 2-bromo-4-fluoro-benzoic acid | 1-(2-carboxy-5-fluorophenyl)-4-(2,5-dibromophenyl)imidazole |
| 16 | 4-fluorophenyl | 2-bromo-4-iodo-benzoic acid | 1-(2-carboxy-5-iodophenyl)-4-(4-fluorophenyl)imidazole |
| 17 | 3,4-dichlorophenyl | 2,4-dibromo-benzoic acid | 1-(2-carboxy-5-bromophenyl)-4-(3,4-dichlorophenyl)-imidazole |
| 18 | 4-n-amylphenyl | 2-bromo-4-methoxy-benzoic acid | 1-(2-carboxy-5-methoxyphenyl)-4-(4-n-amylphenyl)imidazole |
| 19 | 4-isopropylphenyl | 2-bromo-4-trifluoromethylbenzoic acid | 1-(2-carboxy-5-trifluorophenyl)-4-(4-isopropylphenyl)imidazole |
| 20 | 3-trifluoromethyl-4-chlorophenyl | 2-bromobenzoic acid | 1-(2-carboxyphenyl)-4-(3-trifluoromethyl-4-chlorophenyl)-imidazole |
| 21 | 4-nitrophenyl | 2-bromo-4-nitrobenzoic acid | 1-(2-carboxy-5-nitrophenyl)-4-(4-nitrophenyl)imidazole |
| 22 | 4-methylthiophenyl | 2-bromo-4-methylthio-benzoic acid | 1-(2-carboxy-5-methylthiophenyl)-4-(4-methylthiophenyl)imidazole |
| 23 | 4-trifluoromethoxyphenyl | 2-bromo-4-trifluoromethoxybenzoic acid | 1-(2-carboxy-5-trifluoromethoxyphenyl)-4-(4-trifluoromethoxyphenyl)imidazole |
| 24 | 2,4-difluorophenyl | 2-bromo-3,5-dimethyl-benzoic acid | 1-(2-carboxy-4,6-dimethylphenyl)-4-(2,4-difluorophenyl)imidazole |
| 25 | 4-iodophenyl | 2-bromo-6-ethylbenzoic acid | 1-(2-carboxy-3-ethylphenyl)-4-(4-iodophenyl)imidazole |
| 26 | 4-cyanophenyl | 2-bromo-5-methoxy-benzoic acid | 1-(2-carboxy-4-methoxyphenyl)-4-(4-cyanophenyl)imidazole |
| 27 | 4-acetylphenyl | 2-bromo-5-methoxy-benzoic acid | 1-(2-carboxy-4-methoxyphenyl)-4-(4-acetylphenyl)imidazole |
| 28 | 3-trifluoromethyl-4-nitrophenyl | 2-bromobenzoic acid | 1-(2-carboxyphenyl)-4-(3-trifluoromethyl-4-nitrophenyl)imidazole |
| 29 | 4-trifluoromethylphenyl | 2-bromobenzoic acid | 1-(2-carboxyphenyl)-4-(4-trifluoromethylphenyl)imidazole |
| 30 | 4-bromophenyl | 2-bromobenzoic acid | 1-(2-carboxyphenyl)-4-(4-bromophenyl)imidazole |
| 31 | 2,4-dichlorophenyl | 2-bromobenzoic acid | 1-(2-carboxyphenyl)-4-(2,4-dichlorophenyl)imidazole |
| 32 | 4-t-butylphenyl | 2-bromobenzoic acid | 1-(2-carboxyphenyl)-4-(4-t-butylphenyl)imidazole |
| 33 | 3,4-dimethylphenyl | 2-bromobenzoic acid | 1-(2-carboxyphenyl)-4-(3,4-dimethylphenyl)imidazole |
| 34 | 3-chlorophenyl | 2-bromobenzoic acid | 1-(2-carboxyphenyl)-4-(3-chlorophenyl)imidazole |
| 35 | 3-methylphenyl | 2-bromobenzoic acid | 1-(2-carboxyphenyl)-4-(3-methylphenyl)imidazole |
| 36 | 4-cyanophenyl | 2-bromobenzoic acid | 1-(2-carboxyphenyl)-4-(4-cyanophenyl)imidazole |
| 37 | 4-acetylphenyl | 2-bromobenzoic acid | 1-(2-carboxyphenyl)-4-(4-acetylphenyl)imidazole |
| 38 | 4-methylsulfonylphenyl | 2-bromobenzoic acid | 1-(2-carboxyphenyl)-4-(4-methylsulfonylphenyl)imidazole |
| 39 | 4-dimethylaminophenyl | 2-bromobenzoic acid | 1-(2-carboxyphenyl)-4-(4-dimethylaminophenyl)imidazole |
| 40 | 4-carbamoylphenyl | 2-bromobenzoic acid | 1-(2-carboxyphenyl)-4-(4-carbamoylphenyl)imidazole |
| 41 | 4-sulfamylphenyl | 2-bromobenzoic acid | 1-(2-carboxyphenyl)-4-(4-sulfamylphenyl)imidazole |
| 42 | 3-dimethylaminophenyl | 2-bromobenzoic acid | 1-(2-carboxyphenyl)-4-(3-dimethylaminophenyl)imidazole |
| 43 | 3-methyl-4-dimethylaminophenyl | 2-bromobenzoic acid | 1-(2-carboxyphenyl)-4-(3-methyl-4-dimethylaminophenyl)imidazole |
| 44 | 3-methyl-4-methoxyphenyl | 2-bromo-5-nitrobenzoic acid | 1-(2-carboxy-6-nitrophenyl)-4-(3-methyl-4-methoxyphenyl)-imidazole |
| 45 | 3-chloro-5-trifluoromethylphenyl | 2-bromobenzoic acid | 1-(2-carboxyphenyl)-4-(3-chloro-5-trifluoromethylphenyl)imidazole |
| 46 | 3,5-dichlorophenyl | 2-bromobenzoic acid | 1-(2-carboxyphenyl)-4-(3,5-dichlorophenyl)imidazole |
| 47 | 2-pyridyl | 2-bromobenzoic acid | 1-(2-carboxyphenyl)-4-(2-pyridyl)-imidazole |
| 48 | 4-pyridyl | 2-bromobenzoic acid | 1-(2-carboxyphenyl)-4-(4-pyridyl)- |

Table VII-continued

| Example | 4-Arylimidazole Reactant Ar | Substituted 2-Bromobenzoic Acid | 1-(2-Carboxyaryl)-4-arylimidazole Product |
|---|---|---|---|
| 49 | 1-naphthyl | 2-bromobenzoic acid | 1-(2-carboxyphenyl)-4-(1-naphthyl)imidazole |
| 50 | 2-furyl | 2-bromobenzoic acid | 1-(2-carboxyphenyl)-4-(2-furyl)imidazole |
| 51 | 2-thienyl | 2-bromobenzoic acid | 1-(2-carboxyphenyl)-4-(2-thienyl)imidazole |
| 52 | 4-biphenylyl | 2-bromobenzoic acid | 1-(2-carboxyphenyl)-4-(4-biphenyl)imidazole |

Reaction of a substituted 2-bromobenzoic acid with a substituted 3-aryl-1,2,4-triazole gives the correspondingly substituted 1-(2-carboxyaryl)-3-aryl-1,2,4-triazoles as summarized in Table VIII.

Table VIII

| Example | 3-Aryl-1,2,4-triazole Reactant Ar | Substituted 2-Bromobenzoic Acid | 1-(2-Carboxyaryl)-3-aryl-1,2,4-triazole Product |
|---|---|---|---|
| 53 | phenyl | 2-bromo-4-methylbenzoic acid | 1-(2-carboxy-5-methylphenyl)-3-phenyltriazole |
| 54 | phenyl | 2-bromo-4-n-propylbenzoic acid | 1-(2-carboxy-5-n-propylphenyl)-3-phenyltriazole |
| 55 | 2-methyl-4-chlorophenyl | 2-bromo-3,5-dichlorobenzoic acid | 1-(2-carboxy-4,6-dichlorophenyl)-3-(2-methyl-4-chlorophenyl)triazole |
| 56 | 2,5-dibromophenyl | 2-bromo-4-fluorobenzoic acid | 1-(2-carboxy-5-fluorophenyl)-3-(2,5-dibromophenyl)triazole |
| 57 | 3,4-dichlorophenyl | 2,4-dibromobenzoic acid | 1-(2-carboxy-5-bromophenyl)-3-(3,4-dichlorophenyl)triazole |
| 58 | 4-isopropylphenyl | 2-bromo-4-trifluoromethylbenzoic acid | 1-(2-carboxy-5-trifluoromethylphenyl)-3-(4-isopropylphenyl)triazole |
| 59 | 3-trifluoromethyl-4-chlorophenyl | 2-bromo-4-methoxybenzoic acid | 1-(2-carboxy-5-methoxyphenyl)-3-(3-trifluoromethyl-4-chlorophenyl)triazole |
| 60 | 4-nitrophenyl | 2-bromo-4-nitrobenzoic acid | 1-(2-carboxy-5-nitrophenyl)-3-(4-nitrophenyl)triazole |
| 61 | 4-methylthiophenyl | 2-bromo-4-methylthiophenylbenzoic acid | 1-(2-carboxy-5-methylthiophenyl)-3-(4-methylthiophenyl)triazole |
| 62 | 4-trifluoromethoxyphenyl | 2-bromo-4-trifluoromethoxybenzoic acid | 1-(2-carboxy-5-trifluoromethoxyphenyl)-3-(4-trifluoromethoxyphenyl)triazole |
| 63 | 2,4-difluorophenyl | 2-bromo-3,5-dimethylbenzoic acid | 1-(2-carboxy-4,6-dimethylphenyl)-3-(2,4-difluorophenyl)triazole |
| 64 | 4-iodophenyl | 2-bromo-6-ethylbenzoic acid | 1-(2-carboxy-3-ethylphenyl)-3-(4-iodophenyl)triazole |
| 65 | 4-cyanophenyl | 2-bromo-4-n-butylbenzoic acid | 1-(2-carboxy-5-n-butylphenyl)-3-(4-cyanophenyl)triazole |
| 66 | 4-acetylphenyl | 2-bromo-4-isopropylbenzoic acid | 1-(2-carboxy-5-isopropylphenyl)-3-(4-acetylphenyl)triazole |
| 67 | 3-trifluoromethyl-4-nitrophenyl | 2-bromo-4-iodobenzoic acid | 1-(2-carboxy-5-iodophenyl)-3-(3-trifluoromethyl-4-nitrophenyl)triazole |
| 68 | 4-trifluoromethylphenyl | 2-bromo-4-methylthiobenzoic acid | 1-(2-carboxy-5-methylthiophenyl)-3-(4-trifluoromethylphenyl)triazole |
| 69 | 4-bromophenyl | 2-bromobenzoic acid | 1-(2-carboxyphenyl)-3-(4-bromophenyl)triazole |
| 70 | 2,4-dichlorophenyl | 2-bromobenzoic acid | 1-(2-carboxyphenyl)-3-(2,4-dichlorophenyl)triazole |
| 71 | 3,4-dimethylphenyl | 2-bromobenzoic acid | 1-(2-carboxyphenyl)-3-(3,4-dimethylphenyl)triazole |
| 72 | 3-chlorophenyl | 2-bromobenzoic acid | 1-(2-carboxyphenyl)-3-(3-chlorophenyl)triazole |
| 73 | 4-methylsulfonyl | 2-bromobenzoic acid | 1-(2-carboxyphenyl)-3-(4-methylsulfonylphenyl)triazole |
| 74 | 4-dimethylaminophenyl | 2-bromobenzoic acid | 1-(2-carboxyphenyl)-3-(4-dimethylaminophenyl)triazole |
| 75 | 4-carbamoylphenyl | 2-bromobenzoic acid | 1-(2-carboxyphenyl)-3-(4-carbamoylphenyl)triazole |
| 76 | 4-sulfamylphenyl | 2-bromobenzoic acid | 1-(2-carboxyphenyl)-3-(4-sulfamylphenyl)triazole |
| 77 | 3-dimethylaminophenyl | 2-bromobenzoic acid | 1-(2-carboxyphenyl)-3-(3-dimethylaminophenyl)triazole |
| 78 | 3-methyl-4-methoxyphenyl | 2-bromobenzoic acid | 1-(2-carboxyphenyl)-3-(3-methyl-4-methoxyphenyl)triazole |
| 79 | 3-chloro-5-trifluoromethylphenyl | 2-bromobenzoic acid | 1-(2-carboxyphenyl)-3-(3-chloro-5-trifluoromethylphenyl)triazole |
| 80 | 3,5-dichlorophenyl | 2-bromobenzoic acid | 1-(2-carboxyphenyl)-3-(3,5-dichlorophenyl)triazole |
| 81 | 3-pyridyl | 2-bromobenzoic acid | 1-(2-carboxyphenyl)-3-(3-pyridyl)triazole |
| 82 | 2-naphthyl | 2-bromobenzoic acid | 1-(2-carboxyphenyl)-3-(2-naphthyl)triazole |
| 83 | 3-furyl | 2-bromobenzoic acid | 1-(2-carboxyphenyl)-3-(3-furyl)triazole |

Table VIII-continued

| Example | 3-Aryl-1,2,4-triazole Reactant Ar | Substituted 2-Bromobenzoic Acid | 1-(2-Carboxyaryl)-3-aryl-1,2,4-triazole Product |
|---|---|---|---|
| 84 | 3-thienyl | 2-bromobenzoic acid | 1-(2-carboxyphenyl)-3-(3-thienyl)-triazole |
| 85 | 3-biphenylyl | 2-bromobenzoic acid | 1-(2-carboxyphenyl)-3-(3-biphenylyl)triazole |

Utility

The imidazole and triazole carboxylic acids of the invention are useful for the preparation of buffer solutions.

EXAMPLE A

The selected acids listed in Table IX (65–84 mg samples, weighed accurately) were respectively dissolved in a mixture of dimethylsulfoxide (25 ml) and water (10–25 ml) and titrated against 0.09995N aqueous sodium hydroxide using an automatic titrimeter (Metrohm Potentiograph Model E 336). The $pK_a$'s were measured from the half neutralization point on the titration curve, and are listed in Table IX. According to the general theory of buffer solutions (A. I. Vogel, "A Textbook of Quantitative Inorganic Analysis, Theory and Practice," Longmans, Green, London (1948)), the following relationship exists in a dilute solution (0.05–0.2M) of a weak acid to which small additions of acid or base are made $$pH = pK_a + \log [Salt]/[Acid]$$

The pH of the solution is mainly determined by the $pK_a$ of the acid, and in general the buffering capacity (ability to withstand pH change upon addition of acid or base) is maintained within the range 1 acid:10 salt to 10 acid:1 salt, a hundred-fold variation of concentration, or a change of two pH units. The buffer ranges of each of the acids is shown in the third column of Table IX. The acids are useful as buffers in weakly acidic solutions.

Table IX pK_a Values of Selected Acids

Triazoles

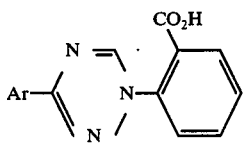

Table IX-continued pK_a Values of Selected Acids

| Ar | $pK_a$ | Buffer Range (pH Units) |
|---|---|---|
| $C_6H_5$ | 5.91 | 4.9 – 6.9 |
| $4\text{-}CH_3OC_6H_4$ | 4.73 | 3.7 – 5.7 |
| $4\text{-}ClC_6H_4$ | 5.48 | 4.5 – 6.5 |
| $3,4\text{-}Cl_2C_6H_3$ | 6.19 | 5.2 – 7.2 |
| $4\text{-}CH_3C_6H_4$ | 4.81 | 3.8 – 5.8 |

Imidazoles

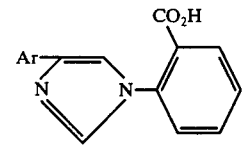

| Ar | $pK_a$ | Buffer Range (pH Units) |
|---|---|---|
| $C_6H_5$ | 4.91 | 3.9 – 5.9 |
| $4\text{-}CH_3OC_6H_4$ | 5.08 | 4.1 – 6.1 |
| $4\text{-}CH_3C_6H_4$ | 5.59 | 4.6 – 6.6 |

The picrate salts of the imidazole and triazole carboxylic acids of the invention are useful dyes for selected natural and synthetic fibers.

EXAMPLE B

Fifty-milligram samples of each of the carboxylic acids were dissolved in the minimum volume (5–20 ml) of warm ethanol and treated with a solution of picric acid (50 mg) in warm ethanol (~1 ml). The solutions were diluted with an equal volume of water and strips of cloth swatch were immersed in them. These mixtures were held in a water bath at 90° for 10 min, and then the swatches were rinsed with cold water and air-dried. The swatches consist of a woven piece of fabric of total width 12 cm in which thirteen different fibers are incorporated in consecutive strips, each strip being approximately 0.9 cm in width. The fibers and the results on dyeing them with the above mixture are shown in Table X. Visual evaluations are (++) strongly dyed, (+) moderately dyed, and (−) very weakly or not dyed at all.

Table X

| | Acetate | Acrilan 1656 | Arnel | Cotton | Creslan 61 | Dacron® 54 | Dacron® 64 | Nylon | Orlon® | Silk | Verel 75 | Viscose | Wool |
|---|---|---|---|---|---|---|---|---|---|---|---|---|---|

1,2,4-Triazole Picrates

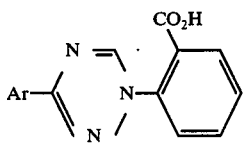

| | Acetate | Acrilan 1656 | Arnel | Cotton | Creslan 61 | Dacron® 54 | Dacron® 64 | Nylon | Orlon® | Silk | Verel 75 | Viscose | Wool |
|---|---|---|---|---|---|---|---|---|---|---|---|---|---|
| Ar = $C_6H_5$ | + | + | − | − | − | − | − | ++ | − | ++ | + | + | ++ |
| Ar = $4\text{-}CH_3OC_6H_4$ | + | + | − | − | − | − | − | ++ | − | ++ | − | − | ++ |
| Ar = $4\text{-}ClC_6H_4$ | + | + | − | − | − | − | − | ++ | − | ++ | − | − | ++ |
| Ar = $3,4\text{-}Cl_2C_6H_4$ | + | + | − | − | − | − | − | ++ | − | ++ | + | − | ++ |
| Ar = $4\text{-}CH_3C_6H_4$ | + | + | − | − | − | − | − | ++ | − | ++ | + | − | ++ |

Imidazole Picrates

Table X-continued

| | Acetate | Acrilan 1656 | Arnel | Cotton | Creslan 61 | Dacron® 54 | Dacron® 64 | Nylon | Orlon® | Silk | Verel 75 | Viscose | Wool |
|---|---|---|---|---|---|---|---|---|---|---|---|---|---|
| Ar—CO$_2$H structure with N-N imidazole ring | | | | | | | | | | | | | |
| Ar = C$_6$H$_5$ | + | + | − | − | − | − | − | ++ | − | ++ | − | − | ++ |
| Ar = 4-CH$_3$OC$_6$H$_4$ | + | + | − | − | − | − | − | ++ | − | ++ | − | − | ++ |
| Ar = 4-CH$_3$C$_6$H$_4$ | + | + | − | − | − | − | − | ++ | − | ++ | − | − | ++ |

The imidazole and triazole compounds of the invention are useful as plant growth modifiers when applied to plants. The compounds are applied to the immediate area where the plant is developing and growing, including preemergence and postemergence application.

Low rates of application of the active ingredient from 0.0028 to 0.9 kilogram per hectare (k/ha) provide a means for regulating the growth of plants: e.g., growth retardation, epinasty, delayed flowering, preventing of fruit set, carbohydrate enrichment and control of axillary growth. At higher rates of application from 11 to 45 kilograms per hectare, compounds of the invention exhibit herbicidal activity on some plant species under specific growth conditions. However, on other plant species the compounds are herbicidal at a rate of 2.3 kilograms per hectare or even lower. The actual amount of active ingredient used, of course, must depend on the particular situation, i.e., the actual plant species, its vigor, the time of year and the condition of the soil.

Growth regulant compositions comprise a plant growth regulating amount of a compound of this invention and a carrier, generally with one or more surface-active agents.

The surface-active agent can be a wetting, dispersing or an emulsifying agent which will assist dispersion of the active compound. The surface-active agent or surfactant can include such anionic, cationic and nonionic agents as have heretofore been generally employed in plant control compositions. Suitable surface-active agents are set out, for example in Searle U.S. Pat. No. 2,426,417; Todd U.S. Pat. No. 2,655,447; Jones U.S. Pat. No. 2,412,510; or Lenher U.S. Pat. No. 2,139,276. A detailed list of such agents is set forth in "Detergents and Emulsifiers Annual" (1965) by John W. McCutcheon, Inc.

In general, less than 10 percent by weight of the surface-active agents will be used in compositions of this invention and ordinarily the amount of surface-active agents will range from 1-5 percent but may even be less than 1 percent by weight.

Plant growth regulant compositions can contain, in addition to a surfactant, finely divided inert diluents such as talcs, natural clays including atapulgite clay and kaolinite clay, pyrophyllite, diatomaceous earths, synthetic fine silicas, calcium silicate, carbonates, calcium phosphates, sulfur, lime and such flours as walnut shell, wheat, redwood, soybean and cottonseed.

The amount of the finely divided inert solid diluent can vary widely but will generally range from 10 to 98 percent by weight of the growth retardant composition. The particle size can vary considerably but will ordinarily be somewhat under 50 microns in the finished formulation. Such compositions are prepared by blending the ingredients and grinding in a hammer mill or in an air attrition mill or similar device until uniform powders are obtained which have a particle size smaller than 50 microns. Compositions containing a surface-active agent and a solid inert diluent are preferably wettable powders containing from 25 to 90 percent of the imidazole or triazole compound.

The compounds can also be formulated as high strength compositions in which the active ingredient can be present in amounts ranging from 90–99 percent. The remainder of the composition comprises surface-active agents, preferably in amounts of from 0.2 to 2 percent and diluents, as described above. Such compositions are prepared by blending and grinding the ingredients to obtain a homogeneous powder of fine particle size.

Compositions of these plant growth regulants and inert solid diluents can also be formulated into granules and pellets. In such compositions, the diluent will generally range from 65 to 99 percent and the active ingredient can range from 1 to 35 percent. They can also be used in the preparation of suspension concentrates, e.g., water extendable emulsifiable oil concentrates.

The compound of Example 1, 1-(2-carboxyphenyl)-4-phenylimidazole containing 1 mole of dimethylsulfoxide of crystallization, showed a very strong hormonal effect (epinastic response) in preemergence tests at 2k/ha toward corn, soybeans, wheat, rice, barnyard grass, morning glory, cocklebur and cassia. The emergence of soybean, wild oats, crabgrass, and nutsedge was inhibited. In postemergence tests at 2k/ha, an epinastic response was shown toward bush beans, sorghum, corn, soybeans, wheat, wild oats, rice, morning glory, cocklebur and cassia. The growth of nutsedge was retarded.

The compounds of Examples 2 and 4, i.e., 1-(2-carboxyphenyl)-4-(4-chlorophenyl)imidazole and 1-(2-carboxyphenyl)-4-(4-methylphenyl)imidazole, showed very strong epinastic responses in preemergence tests at 2k/ha toward corn, soybeans, rice and crabgrass. Toward sorghum, wheat and wild oats, the compound of Example 2 showed a very strong response and the compound of Example 4 a moderate to strong response. In postemergence tests both compounds showed an epinastic response (2k/ha) toward cotton, bush beans, sorghum, corn, and morning glory, and they both showed strong axillary stimulation of soybeans.

The compound of Example 3, 1-(2-carboxyphenyl)-4-(4-methoxyphenyl)imidazole, in postemergence tests at 2k/ha, showed an epinastic response toward bush beans, cotton, sorghum, corn, soybeans, ice, cocklebur and cassia. It also showed axillary stimulation of soybeans, barnyard grass and cassia.

In a similar way the triazoles of the invention are plant growth modifiers. The compound of Example 5, 1-(2-carboxyphenyl)-3-phenyl-1,2,4-triazole, showed an epinastic response in postemergence tests, 2k/ha, toward sorghum, rice, soybeans, and nutsedge, and the growth of wheat, wild oats, and barnyard grass was retarded.

The compounds of Examples 6, 7, and 8, i.e., 1-(2-carboxyphenyl)-3-(4-chlorophenyl)-1,2,4-triazole, 1-(2-carboxyphenyl)-3-(3,4-dichlorophenyl)-,2,4-triazole, and 1-(2-carboxyphenyl)-3-(4-methoxyphenyl)-1,2,4-triazole, showed epinastic responses in preemergence tests, 2k/ha, toward nutsedge, cassia, rice, wheat, wild oats, sorghum and corn.

The compound of Example 9, 1-(2-carboxyphenyl)-3-(4-methylphenyl)-1,2,4-triazole, in both preemergence and postemergence tests at 2k/ha, showed an epinastic response toward sorghum, rice, morning glory, cocklebur, cassia and nutsedge. The growth of bush beans was retarded in post-emergence tests.

I claim:
1. A compound of the formula

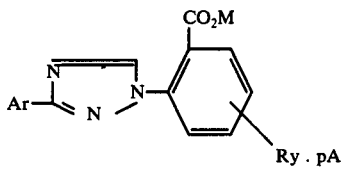

in which
Ar is phenyl, naphthyl, biphenylyl, pyridyl, furyl, thienyl or phenyl substituted with up to two of fluorine, chlorine, bromine, iodine, alkyl of 1–5 carbons, methoxyl, trifluoromethyl, nitro, methylthio, trifluoromethoxyl, dimethylamino, cyano, acetyl, methylsulfonyl, carbamoyl or sulfamyl;
R is hydrogen, fluorine, chlorine, bromine, iodine, methoxyl, trifluoromethyl, nitro, methylthio, trifluoromethoxyl or alkyl of 1–5 carbon atoms;
$p$ is 0 or 1;
$y$ is 1 or 2;
A is an acid;
M is hydrogen, sodium, potassium, lithium, calcium or magnesium; with the proviso that when M is other than hydrogen, $p$ is 0.

2. A compound of claim 1 wherein Ar is phenyl, 4-chlorophenyl, 4-methoxyphenyl, 4-methylphenyl or 3,4-dichlorophenyl.

3. A compound of claim 1 wherein M is hydrogen or alkali metal and R is hydrogen.

4. The compound of claim 1 which is 1-(2-carboxyphenyl)-3-phenyl-1,2,4-triazole.

5. The compound of claim 1 which is 1-(2-carboxyphenyl)-3-(4-chlorophenyl)-1,2,4-triazole.

6. The compound of claim 1 which is 1-(2-carboxyphenyl)-3-(3,4-dichlorophenyl)-1,2,4-triazole.

7. The compound of claim 1 which is 1-(2-carboxyphenyl)-3-(4-methoxyphenyl)-1,2,4-triazole.

8. The compound of claim 1 which is 1-(2-carboxyphenyl)-3-(4-methylphenyl)-1,2,4-triazole.

9. A composition comprising a carrier and a plant growth retarding amount of a compound of claim 1.

10. A composition comprising a carrier and a plant growth retarding amount of a compound of claim 2.

11. A composition comprising a carrier and a plant growth retarding amount of a compound of claim 3.

12. A composition comprising a carrier and a plant growth retarding amount of a compound of claim 4.

13. A composition comprising a carrier and a plant growth retarding amount of a compound of claim 5.

14. A composition comprising a carrier and a plant growth retarding amount of a compound of claim 6.

15. A composition comprising a carrier and a plant growth retarding amount of a compound of claim 7.

16. A composition comprising a carrier and a plant growth retarding amount of a compound of claim 8.

17. The process of regulating plant growth comprising the step of applying to the plant a plant growth retarding amount of a compound of claim 1.

18. The process of regulating plant growth comprising the step of applying to the plant a plant growth retarding amount of a compound of claim 2.

19. The process of regulating plant growth comprising the step of applying to the plant a plant growth retarding amount of a compound of claim 3.

20. The process of regulating plant growth comprising the step of applying to the plant a plant growth retarding amount of a compound of claim 4.

21. The process of regulating plant growth comprising the step of applying to the plant a plant growth retarding amount of a compound of claim 5.

22. The process of regulating plant growth comprising the step of applying to the plant a plant growth retarding amount of a compound of claim 6.

23. The process of regulating plant growth comprising the step of applying to the plant a plant growth retarding amount of a compound of claim 7.

24. The process of regulating plant growth comprising the step of applying to the plant a plant growth retarding amount of a compound of claim 8.